(12) United States Patent
Liu

(10) Patent No.: US 10,828,277 B2
(45) Date of Patent: Nov. 10, 2020

(54) ANTIOXIDANT COMPLEX FOR REDUCING NUMBER OF SOMATIC CELL IN LIVESTOCK ANIMAL, AND PREPARATION METHOD AND APPLICATION THEREOF

(71) Applicant: CHINA AGRICULTURAL UNIVERSITY, Beijing (CN)

(72) Inventor: Guoshi Liu, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 15/540,002

(22) PCT Filed: Dec. 18, 2015

(86) PCT No.: PCT/CN2015/097907
§ 371 (c)(1),
(2) Date: Jun. 26, 2017

(87) PCT Pub. No.: WO2016/131333
PCT Pub. Date: Aug. 25, 2016

(65) Prior Publication Data
US 2017/0348281 A1     Dec. 7, 2017

(30) Foreign Application Priority Data
Feb. 16, 2015   (CN) .......................... 2015 1 0085041

(51) Int. Cl.
*A61K 31/375*     (2006.01)
*A61K 31/4045*    (2006.01)
*A61K 9/00*       (2006.01)
*A61K 47/10*      (2017.01)
*A01J 7/04*       (2006.01)
*A61K 39/39*      (2006.01)
*A61K 45/06*      (2006.01)
(Continued)

(52) U.S. Cl.
CPC ............... *A61K 31/375* (2013.01); *A01J 7/04* (2013.01); *A61K 9/0019* (2013.01); *A61K 31/4045* (2013.01); *A61K 39/39* (2013.01); *A61K 45/06* (2013.01); *A61K 47/10* (2013.01); *A01K 29/00* (2013.01); *A61K 38/17* (2013.01); *A61K 2039/55511* (2013.01)

(58) Field of Classification Search
CPC .... A61K 31/375; A61K 31/4045; A61P 15/14
See application file for complete search history.

(56) References Cited

FOREIGN PATENT DOCUMENTS

CN     104784171 A     7/2015

OTHER PUBLICATIONS

Jiménez et al.; "Effect of melatonin implants on somatic cell counts in dairy goats"; 2009; Small Ruminant Research; 84: 116-120 (Year: 2009).*

(Continued)

*Primary Examiner* — Timothy P Thomas
(74) *Attorney, Agent, or Firm* — Nixon & Vanderhye P.C.

(57) ABSTRACT

Provided are an antioxidant complex for reducing the number of somatic cells in a livestock animal and a preparation method and application thereof. Active components of the preparation are melatonin (MT) having a centration of 2-30 g/L and vitamin C having a concentration of 1-14.3 g/L. The antioxidant complex provided in the present invention can effectively reduce the number of somatic cells in a diary cow and improve milk quality.

5 Claims, 4 Drawing Sheets

(51) Int. Cl.
  *A01K 29/00* (2006.01)
  *A61K 38/17* (2006.01)
  *A61K 39/00* (2006.01)

(56) References Cited

OTHER PUBLICATIONS

Boulanger et al.; "Protective Effect of Melatonin and Catalase in Bovine Neutrophil-induced Model of Mammary Cell Damage"; 2002; J. Dairy Sci.; 85: 562-569 (Year: 2002).*

Matsui; "Vitamin C in Cattle"; 2012; Asian-Aust. J. Anim. Sci.; 25(5): 597-605 (Year: 2012).*

Scientific Committee on Consumer Safety (SCCS; Opinion on Melatonin; https://ec.europa.eu/health/scientific_committees/consumer_safety/docs/sccs_o_022.pdf; 2010; accessed Mar. 6, 2018 (Year: 2010).*

Auldist et al.; "Effects of melatonin on the yield and composition of milk from grazing dairy cows in New Zealand"; 2006; Journal of Dairy Research; 74:52-57 (Year: 2006).*

Neto et al.; "Solubility of Vitamin C in Water, Ethanol, Propan-1-ol, Water + Ethanol, and Water + Propan-1-ol at (298.15 and 308.15) K"; 2010; J. Chem. Eng. Data; 55: 1718-1721 (Year: 2010).*

PubChem; "Ascorbic Acid"; https://pubchem.ncbi.nlm.nih.gov/compound/54670067#section=Solubility, accessed Mar. 6, 2018 (Year: 2010).*

Dairy Herd Management; "Move Injections to the Neck"; https://www.dairyherd.com/article/move-injections-neck; 2012; accessed Apr. 9, 2019 (Year: 2012).*

Sharma et al.; "Relationship of Somatic Cell Count and Mastitis: An Overview"; 2011; Asian-Aust. J. Anim. Sci.; 24(3): 429-438 (Year: 2011).*

Akbulut et al., "The Effects of Melatonin on Humoral Immune Responses of Young and Aged Rats," Immunological Investigations, 2001, pp. 17-20, vol. 30, No. 1.

Carrillo-Vico et al., "Melatonin: Buffering the Immune System," International Journal of Molecular Sciences, 2013, pp. 8638-8683, vol. 14.

Farez et al., "Melatonin Contributes to the Seasonality of Multiple Sclerosis Relapses," Cell, Sep. 2015, pp. 1338-1352, vol. 162.

Haldar et al., "Pineal Modulation of Thymus and Immune Function in a Seasonally Breeding Tropical Rodent, *Funambulus pennanti*," Journals of Experimental Zoology, 2001, pp. 90-98, vol. 289.

Maestroni, "The Immunotherapeutic Potential of Melatonin," Exp. Opin, Invest. Drugs, Ashley Publications Ltd., 2001, pp. 467-476, vol. 10, No. 3.

Paredes et al., "Melatonin: Helping Cells Cope With Oxidative Disaster," Cell Membranes and Free Radical Research, Dec. 2010, pp. 99-111, vol. 2, No. 3.

Singh et al. "Melatonin and Differential Effect of L-thyroxine on Immune System of Indian Tropical Bird *Perdicula asiatica*," General and Comparative Endocrinology, 2006, pp. 215-221, vol. 145.

Tong et al., "Experimental Study on the Effect of Melatonin and Vitamin C on Lipid Peroxidization Reaction in Severe Acute Pancreatitis," Chin J Pancreatol, Apr. 2007, pp. 116-118, vol. 7, No. 2.

* cited by examiner

ANTIOXIDANT COMPLEX FOR REDUCING NUMBER OF SOMATIC CELL IN LIVESTOCK ANIMAL, AND PREPARATION METHOD AND APPLICATION THEREOF

TECHNICAL FIELD

The present invention relates to the field of animal husbandry and veterinary medicine, in particular to a compound antioxidant preparation for reducing the number of somatic cells in a livestock animal and a preparation method and application thereof.

BACKGROUND ART

Dairy cow mastitis, also known as bovine mastitis, is the most common disease of dairy cows, and it is mainly caused by chemical, physical, microbial and other stimulations and invasions to dairy cow breast, which lead to mechanical barrier of body and immune system abnormalities. Dairy cow mastitis not only produces some damage and influence on the cow body and mental state, but also reduces the milk production of dairy cows and the contents of lactoprotein, lactose and fat in milk. According to reports, the National Mastitis Council (U.S.) estimates that the loss caused by mastitis is 225 dollars/cow each year in United States, and 26.5% of dairy cows are eliminated because of mastitis. In Finland, Norway and Athens, dairy cows eliminated due to breast health problems account for 35%, 19% and 22%, respectively. In China, the reported positive rate of dairy cow mastitis is between 46.4% and 85.7%, and the positive rate in udder region is between 28% and 59%. Generally, incidence rate of subclinic mastitis reaches 20%-40% or more, even up to 50%-80%. In recent years, the incidence rate of dairy cow subclinic mastitis has been on the rise. The loss of milk production caused by dairy cow mastitis is about 3.8 million tons in the world each year. Whether or not pathogenic microorganisms can cause mastitis after invading the breast depends on the virulence of pathogens, and is also closely related with autoimmunity of the body.

Melatonin (MT) is a neuroendocrine hormone produced by pineal glands of mammalians and human, and has good antioxidant and body immunity-modulating functions. Since 1980s when it was found that melatonin has modulatory effect on immune system, the influence of melatonin on the body immune function has attracted more and more attention. The white blood cell number, the percentage of lymphocytes and the phagocytic index of neutrophils in plasma of mice were decreased significantly by increased illumination, but after exogenous injection of melatonin, all of the white blood cell number, the percentage of lymphocytes and the phagocytic index of neutrophils were significantly increased. In rats which were exposed to continuous illumination and had pineal body removed, the number of neutrophils in serum was decreased, and the circadian rhythm of adhesion and phagocytosis disappeared. Melatonin also has important influence on humoral immunity in addition to the influence on cellular immune function of the body. In older mice injected with melatonin, the serum IgM and IgG were significantly increased compared to normal control group, thymus and spleen were significantly increased in weight, and the number and activity of T and B lymphocytes and NK cell were also enhanced accordingly. Application of the present invention can reduce the number of somatic cells of high-production dairy cows having the number of somatic cells from 300,000 to 1,000,000/mL by 50% or more, and the reduction is significantly higher than those caused by vitamin E, vitamin C, tea polyphenols (13.9%, L I U Shijun, et. al., 2010) and other biological antioxidant preparations. In this study, a compound antioxidant preparation consisting of melatonin and vitamin C (Vc) was applied to a research on enhancing body immunity of dairy cows, melatonin concentration in the body of dairy cows was increased by means of subcutaneous injection, influence of the compound antioxidant preparation on the number of somatic cells of normal dairy cows was studied, and body immunity was enhanced so as to achieve the purpose of reducing the number of somatic cells, improving health degree of dairy cows and improving milk quality.

SUMMARY OF THE INVENTION

An object of the present invention is to provide a compound antioxidant preparation for reducing the number of somatic cells in a livestock animal and its preparation method and application.

To achieve the object of the present invention, the technical solution of the present invention is as follows:

A compound antioxidant preparation for reducing the number of somatic cells in a livestock animal is in form of injection, and comprises melatonin and vitamin C as active components.

Further, the concentration of the melatonin is 2 g/L-30 g/L.

Preferably, the concentration of the melatonin is 2.32 g/L.

Further, the concentration of the vitamin C is 1 g/L-14.3 g/L.

Preferably, the concentration of the vitamin C is 8.8 g/L.

Still further, adjuvant of the preparation is 75% ethanol solution.

The present invention further provides a method of preparing the preparation, and the method comprises: dissolving vitamin C in 75% ethanol solution followed by addition of melatonin, wherein, the whole operation process needs to be carried out in a dark room (protected from light).

The invention also provides the use of the preparation in improving the milk quality of a livestock animal.

The livestock animal is a dairy cow, a dairy-beef dual-purpose cattle, or a dairy goat; preferably a dairy cow.

In an embodiment of the present invention, Chinese Holstein cows are studied.

The present invention has the following beneficial effects:

In the present invention, it is found by animal experiments that the number of somatic cells in the sample of milk produced by Holstein cow is decreased by subcutaneously injecting 2 mL of the compound antioxidant preparation of the present invention at the neck of dairy cows for 4 days continuously, which provides beneficial reference for further study on decrease of the number of somatic cells of dairy cows by antioxidant preparation.

The active components of the compound antioxidant preparation provided in the present invention are melatonin and vitamin C which are natural and innocuous, and thus there is no problem of residue of veterinary drugs, withdrawal period and withdrawal period for milk. This not only saves production cost, but also reduces the workload of cattle farm staff.

When the number of somatic cells of dairy cow is higher than 100,000/ml, the number of somatic cells in milk can be significantly reduced by about 50% by using the compound antioxidant provided in the present invention, which fully demonstrates that the compound antioxidant preparation of the present invention can effectively decrease the number of somatic cells of dairy cow.

BEST MODE OF THE INVENTION

Figure 1:
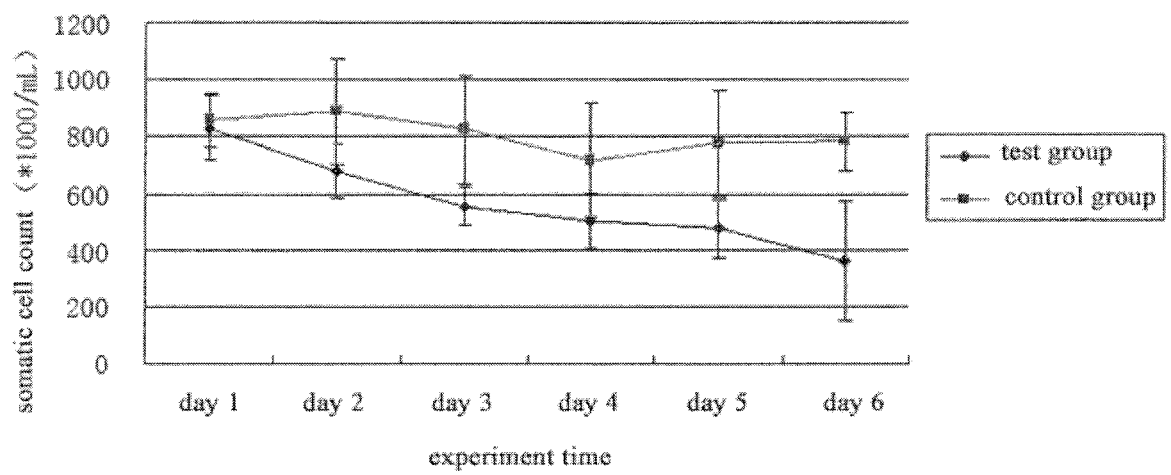
FIG. 1 shows a curve of the somatic cell count change in 1-6 days after injection of a compound antioxidant preparation into dairy cows having a somatic cell count of 600,000-1,000,000/mL as described in experimental example 1 of the present invention.

The following examples are described for the purpose of illustrating the present invention rather than limiting the scope of the present invention.

The reagents and materials used in the following examples are commercially available.

Melatonin is needed to reach a purity of 99.9%.

Example 1: Compound Antioxidant Preparation and its Preparation Method

Raw Materials: Melatonin and Vitamin C
Preparation method: 880 mg of vitamin C and 232 mg of melatonin were weighed accurately. The 880 mg of vitamin C was dissolved into 75% ethanol solution in a 100 ml volumetric flask, stirred to uniformity, then added with the 232 mg of melatonin, stirred to uniformity and diluted to 100 ml. Finally, the resulting solution was divided into injection doses of 2 ml. All of the operations were carried out in a dark room.

Example 2: Compound Antioxidant Preparation and its Preparation Method

Example 2 is the same as example 1 except that the concentration of melatonin is 2 g/L, and the concentration of vitamin C is 1 g/L.

Example 3: Compound Antioxidant Preparation and its Preparation Method

Example 3 is the same as example 1 except that the concentration of melatonin is 30 g/L, and the concentration of vitamin C is 14.3 g/L.

Experimental Example 1: Application of the Compound Antioxidant Preparation in Decreasing Somatic Cell Count of Dairy Cow and Improving Milk Quality 1. Raw Materials and Method 1.1 Time and Location for Experiments
From Sep. 1, 2013 to Sep. 30, 2013, in a cattle farm with a certain scale, Beijing
1.2 Preparation and Usage of the Compound Antioxidant Preparation
The concentrations of melatonin and vitamin C of the compound antioxidant preparation were 2-30 g/L and 1-14.3 g/L, respectively. Subcutaneous injection at the neck was adopted.
1.3 Experimental Animals
80 Holstein dairy cows with similar lactation days and milk production were chosen, and divided into 4 groups in terms of somatic cell count, i.e. 600,000-1,000,000/mL, 300,000-500,000/mL, 100,000-200,000/mL and 0-100,000/mL groups, each group including 20 dairy cows. All of feeding manner, milking manner and daily management for test cows run according to existing regulations in the cattle farm, i.e. free stall feeding, feeding total mixed rations, free drinking and milking three times in one day were adopted for all test cows.
1.4 Experimental Design
Only the milk obtained from the first milking was sampled every day. 2 ml of the compound antioxidant preparation was injected for 4 days continuously after sampling. At day 5, injection was stopped, and only milk sampling was performed. Milk sampling was continued in subsequent day 6, 8, 10, 13 and 16.
1.5 Determination of Somatic Cell Count
Each of the collected milk samples was added with three drops of saturated potassium dichromate solution, refrigerated at 4° C. in a refrigerator, and then sent to National Dairy Herd Improvement Standard Substance Preparation Laboratory for determination of somatic cell count.
1.6 Data Processing
All experimental data were analyzed by SPSS software.

2 Results and Analysis 2.1 Influence on the Somatic Cell Count Change of Dairy Cows Having a Somatic Cell Count of 600,000-1,000,000/mL by Subcutaneous Injection of the Compound Antioxidant Preparation of Example 1

Figure 2:
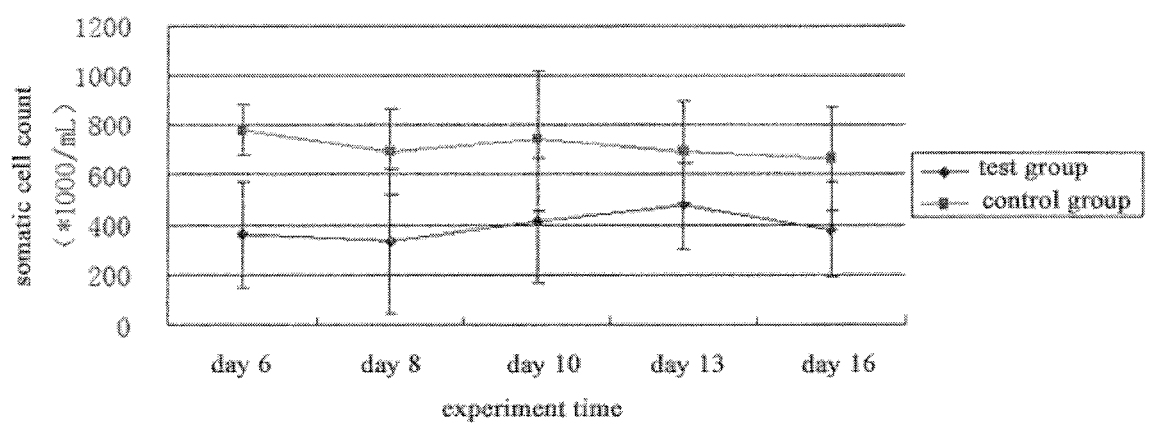
FIG. 2 shows a curve of the somatic cell count change in 6-16 days after injection of a compound antioxidant preparation into dairy cows having a somatic cell count of 600,000-1,000,000/mL as described in experimental example 1 of the present invention.

A curve of the somatic cell count change of dairy cows having a somatic cell count of 600,000-1,000,000/mL after injection of the compound antioxidant preparation is shown in FIG. 1. Somatic cells show a significantly decreasing trend from the day of injection on dairy cows. The decrease degree of the test group is significantly higher than that of the control group, and no increase occurred in the period of injection. The largest decrease is from 757,000/mL before injection to 215,000/mL. However, such decrease does not maintain for a long time, and the somatic cell count of dairy cows returns to an undulate law which is the same as that of the control group soon after the injection of the compound antioxidant preparation is stopped (FIG. 2).

2.2 Influence on the Somatic Cell Count Change of Dairy Cows Having a Somatic Cell Count of 300,000-500,000/mL by Subcutaneous Injection of the Compound Antioxidant Preparation of Example 1

Figure 3:
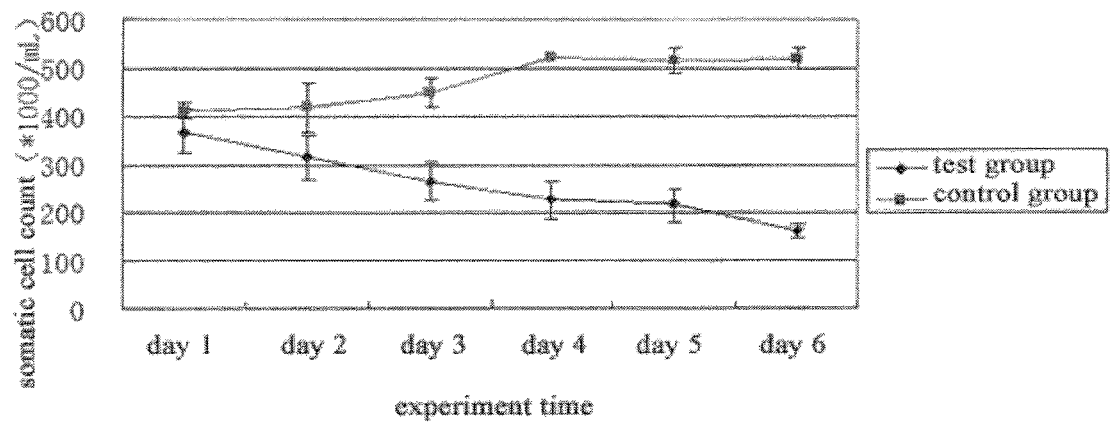
FIG. 3 shows a curve of the somatic cell count change in 1-6 days after injection of a compound antioxidant preparation into dairy cows having a somatic cell count of 300,000-500,000/mL as described in experimental example 1 of the present invention.
Figure 4:
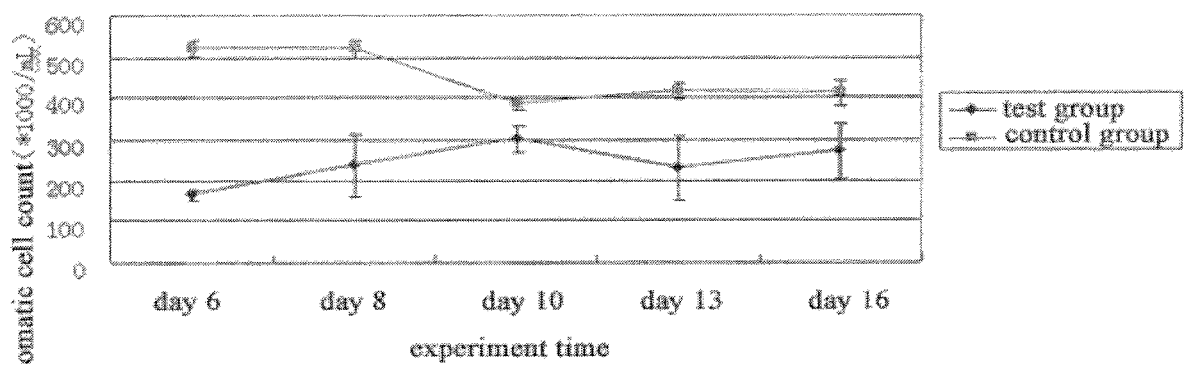
FIG. 4 shows a curve of the somatic cell count change in 6-16 days after injection of a compound antioxidant preparation into dairy cows having a somatic cell count of 300,000-500,000/mL as described in experimental example 1 of the present invention.

A curve of the somatic cell count change of dairy cows having a somatic cell count of 300,000-500,000/mL after injection of the compound antioxidant preparation is shown in FIG. 3. The somatic cell count in dairy cows having a somatic cell count of 300,000-500,000/mL shows a continuously decreasing trend after continuous injection of the compound antioxidant preparation, which is in stark contrast to the increasing trend of the control group. The largest decrease is from 375,000/mL before injection to 147,000/mL. After the injection of the compound antioxidant preparation is stopped, the somatic cell count of test dairy cows increases slightly, and finally maintains at 200,000-300,000/mL for a long time. On the contrast, the somatic cell count of the dairy cows in the control group shows a decreasing trend at this time, and finally maintains at 300,000-400,000/mL.

2.3 Influence on the Somatic Cell Count Change of Dairy Cows Having a Somatic Cell Count of 100,000-200,000 by Subcutaneous Injection of the Compound Antioxidant Preparation of Example 1

Figure 5:
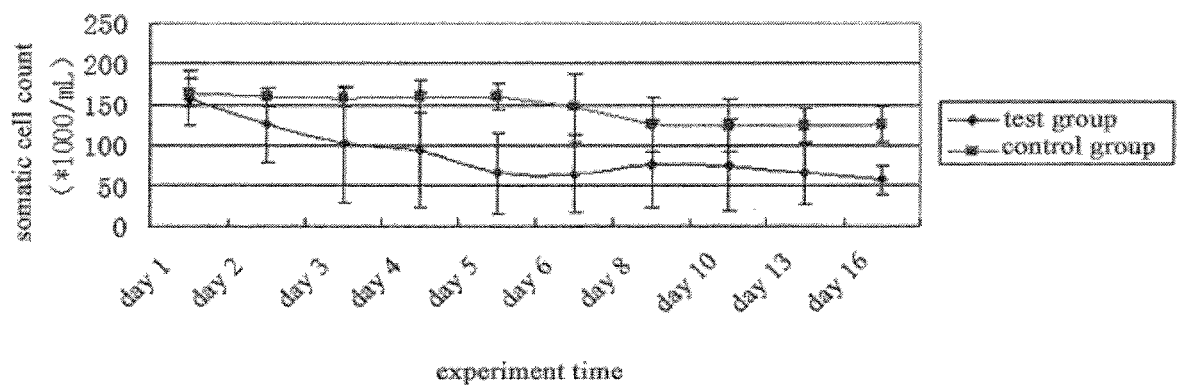
FIG. 5 shows a curve of the somatic cell count change in 1-16 days after injection of a compound antioxidant preparation into dairy cows having a somatic cell count of 100,000-200,000/mL as described in experimental example 1 of the present invention.

A curve of the somatic cell count change of dairy cows having a somatic cell count of 100,000-200,000/mL after injection of the compound antioxidant preparation is shown in FIG. 5. The somatic cell count shows a significantly decreasing trend after the dairy cows having a somatic cell count of 100,000-200,000 are injected with the compound antioxidant preparation. The somatic cell count decreases from 150,000/mL before injection to 60,000/mL after injection, and maintains at 50,000-100,000/mL after the injection is stopped. The somatic cell count of the dairy cows in the control group also shows a decreasing trend, but the decrease is slow; and the somatic cell count finally maintains at 100,000-150,000/mL.

2.4 Influence on the Somatic Cell Count Change of Dairy Cows Having a Somatic Cell Count of 0-100,000/mL by Subcutaneous Injection of the Compound Antioxidant Preparation of Example 1

Figure 6:
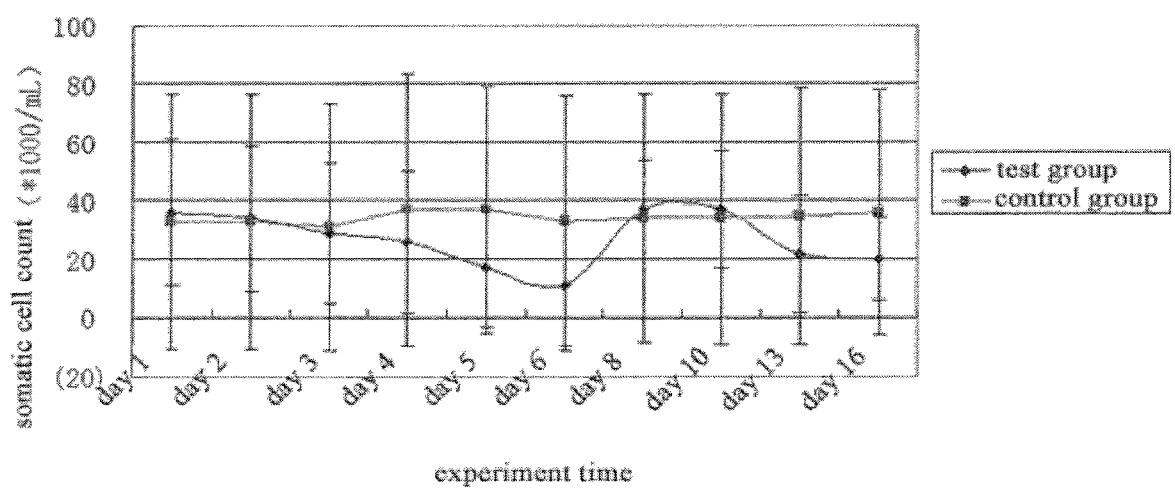
FIG. 6 shows a curve of the somatic cell count change in 1-16 days after injection of a compound antioxidant preparation into dairy cows having a somatic cell count of 0-100,000/mL as described in experimental example 1 of the present invention.

A curve of the somatic cell count change of dairy cows having a somatic cell count of 0-100,000/mL after injection of the compound antioxidant preparation is shown in FIG. 6. After injection of the compound antioxidant preparation, the somatic cell count of dairy cows having a somatic cell count of 0-100,000/mL shows a decreasing trend, but increases obviously after the injection is stopped, and finally maintains at 20,000-40,000/mL. The somatic cell count change of the dairy cows in the control group is relatively small, and maintains at 20,000-40,000/mL all through the experiment.

3. Conclusion

Exogenous injection of an antioxidant preparation can play the role of decreasing somatic cell count of dairy cows, and the role is particularly evident for dairy cows having a somatic cell count of 100,000/mL or more. The modulatory effect of melatonin on body immunity may be the cause of the decrease in somatic cell count of dairy cows. A somatic cell count of 500,000/mL is defined as the benchmark of (clinical) mastitis internationally. Pathogenic microorganisms will cause inflammation in dairy cows after breaking through the first line of defense, i.e. keratin. If neutrophils fail to enter the breast in time, dairy cows may suffer from mastitis. However, whether or not pathogenic microorganisms can cause mastitis after invasion to the breast depends on the virulence of pathogens, and is also closely related with the immunity of the body. Using surfactants, immunomodulators and microbial cell enzymes, Russian scholars developed biological agents, which can treat subclinic mastitis by improving the body immunity of dairy cows and achieve good effect. In recent studies, it has been found that melatonin can increase the weight of immune organs, increase the percentage of lymphocytes in peripheral blood, promote the formation of antibodies and proliferation of T and B lymphocytes, stimulate the production of cytokines, participate in the regulation of neuroendocrine-immune network, and plays an important role in mediating circadian rhythm of immune function.

Comparative Example 1

1. Subcutaneous Injection of a Preparation (2 mL) Comprising Vitamin C and Vitamin E (Ve)

20 Holstein dairy cows having similar lactation days and milk production and a somatic cell count of 600,000-1,000,000/mL were chosen, and divided into 2 groups randomly, i.e. 600,000-1,000,000/mL, each group including 10 dairy cows. All of feeding manner, milking manner and daily management for test cows run according to existing regulations in the cattle farm, i.e. free stall feeding, feeding total mixed rations, free drinking and milking three times in one day were adopted for all test cows. Only the milk obtained from the first milking was sampled every day. 2 ml of the preparation comprising vitamin C and vitamin E was injected for 4 days continuously after sampling. At day 5, injection was stopped, and only milk sampling was performed. And milk sampling was continued in subsequent day 6, 8, 10, 13 and 16. Each of the collected milk samples was added with three drops of saturated potassium dichromate solution, refrigerated at 4° C. in a refrigerator, and then sent to National Dairy Herd Improvement Standard Substance Preparation Laboratory for determination of somatic cell count.

2. Experimental Results

Figure 7:
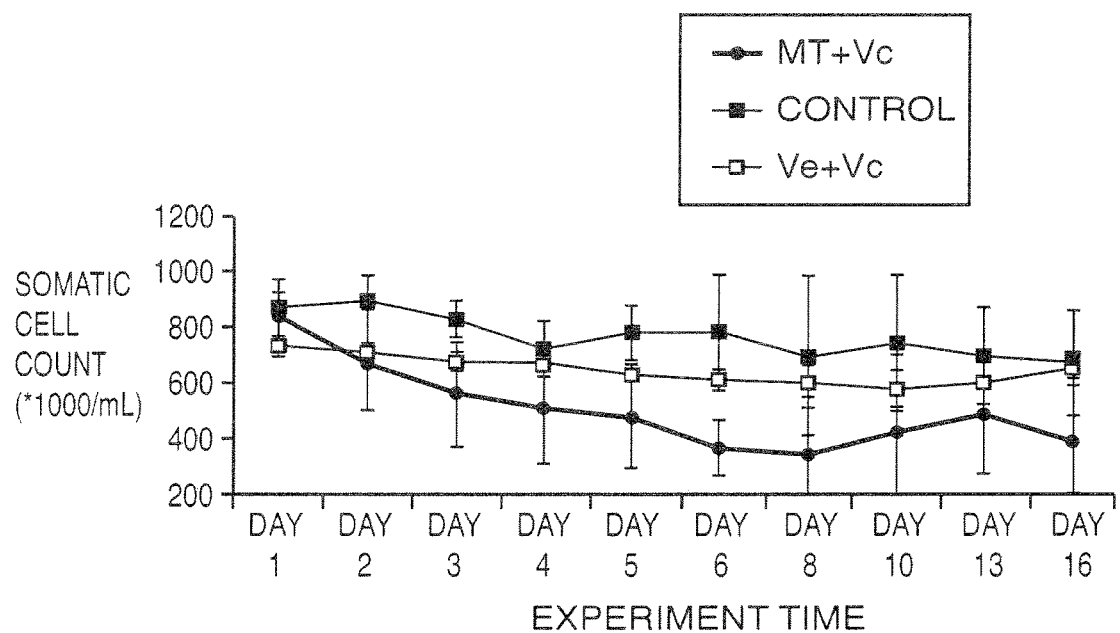
FIG. 7 shows a curve of the somatic cell count change in 1-16 days after subcutaneous injection of a preparation comprising vitamin C and vitamin E (Ve) into dairy cows having a somatic cell count of 600,000-1,000,000/mL as described in comparative example 1 of the present invention.

After injection of the preparation comprising vitamin C and vitamin E, the somatic cell count of dairy cows decreases by about 15%, and the effect is evidently inferior to that of the preparation comprising melatonin and vitamin C. Furthermore, the effect does not maintain for a long time, and an undulate law the same as that of the control group occurs from the $4^{th}$ day after injection is stopped (FIG. 7).

Comparative Example 2

1. Subcutaneous Injection of Preparations (2 mL) Comprising MT and Vc at Different Ratios 40 Holstein dairy cows having similar lactation days and milk production and a somatic cell count of 600,000-1,000, 000/mL were chosen, and divided into 5 groups randomly. Preparations at different ratios as described in the present invention, mainly including 5 kinds, i.e. MT(1 g/L)+Vc(0.5 g/L), MT(1 g/L)+Vc(1 g/L), MT(2.32 g/L)+Vc(8.8 g/L), MT(23.2 g/L)+Vc(14.3 g/L) and MT(50 g/L)+Vc(25 g/L), were injected for 4 days continuously. At day 5, injection was stopped, and only milk sampling was performed. And milk sampling was continued in subsequent day 6, 8, 10, 13 and 16. Each of the collected milk samples was added with three drops of saturated potassium dichromate solution, refrigerated at 4° C. in a refrigerator, and then sent to National Dairy Herd Improvement Standard Substance Preparation Laboratory for determination of somatic cell count.

2. Experimental Results

Figure 8:
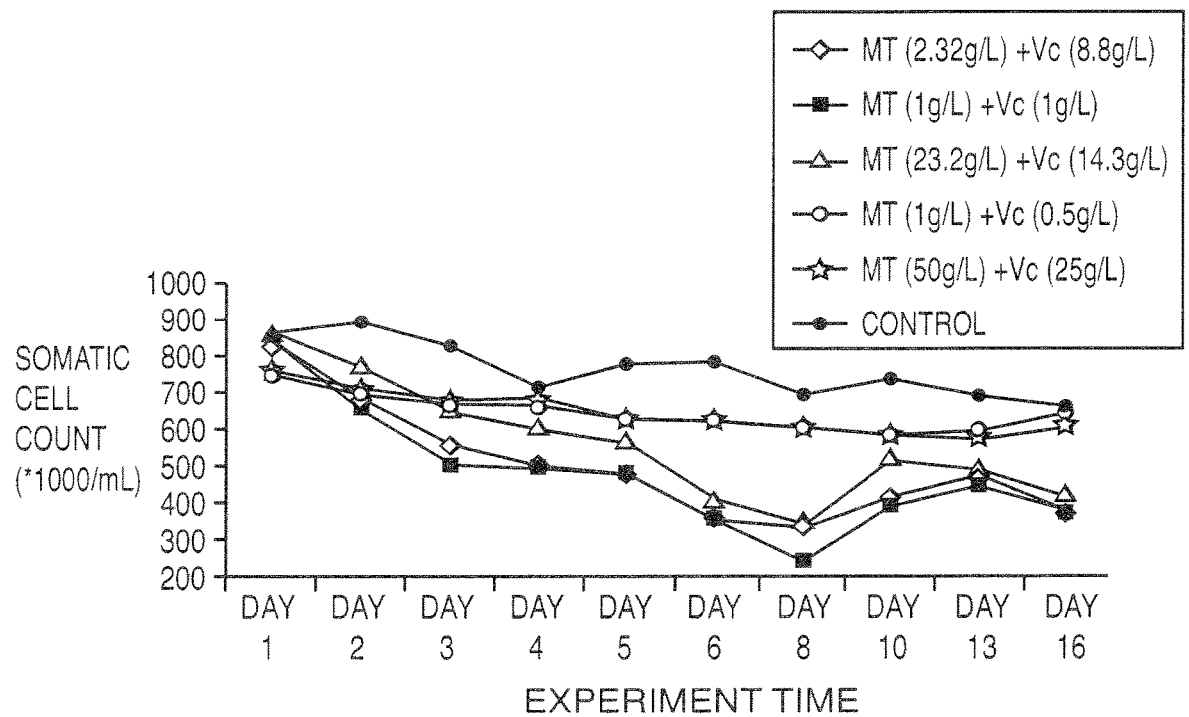
FIG. 8 shows a curve of the somatic cell count change in 1-16 days after subcutaneous injection of preparations of the present invention at different component ratios into dairy cows having a somatic cell count of 600,000-1,000,000/mL as described in comparative example 2 of the present invention.

All of the preparations at different ratios have the function of decreasing somatic cell count of dairy cows, but the effects are highly different. Preparations MT(1 g/L)+Vc(1 g/L), MT(2.32 g/L)+Vc(8.8 g/L) and MT(23.2 g/L)+Vc(14.3 g/L) are substantially consistent in effect, and play the function of significantly decreasing somatic cells of high-production dairy cows with a decrease of about 50%. Preparations MT(1 g/L)+Vc(0.5 g/L) and MT(50 g/L)+Vc(25 g/L) have poor effect in decreasing somatic cell count with a decrease of 5%-16%; and furthermore, the effect does not maintain for a long time, and an undulate law the same as that of the control group starts to occur when injection has been stopped for 4-6 days (FIG. 8).

Although the present invention has been described in detail through the general descriptions and detailed embodiments above, it is obvious to those skilled in the art to make modifications or improvements based on the present invention. Hence, the modifications or improvements which are made without departing from the spirits of the present invention fall into the protection scope claimed by the present invention.

INDUSTRIAL APPLICABILITY

The compound antioxidant preparation for reducing the number of somatic cells in a livestock animal disclosed by the present invention can improve milk quality of a livestock animal. By animal experiments, it is found that somatic cell count in the sample of milk produced by dairy cows is decreased by subcutaneously injecting 2 mL of the compound antioxidant preparation of the present invention at the neck of dairy cows for 4 days continuously, which provides beneficial reference for further study on decrease of somatic cell count of dairy cows by antioxidant preparation. The active components of the compound antioxidant preparation provided in the present invention are melatonin and vitamin C which are natural and innocuous, and thus there is no problem of residue of veterinary drugs, withdrawal period and withdrawal period for milk. This not only saves production cost, but also reduces the workload of cattle farm staff.

What is claimed is:

1. A method of improving milk quality by administering an antioxidant preparation to a dairy cow with a somatic cell count greater than 100,000/mL for reducing the number of somatic cells in the dairy cow, characterized in that the preparation is in a form of an injection and comprises a combination of purified melatonin and vitamin C as active components, wherein four injections are administered at a neck of the dairy cow on four sequential days, wherein the administration comprises injecting 2 mL of the preparation to the dairy cow, wherein the concentration of the purified melatonin in the preparation is 1-23.2 g/L and the concentration of the vitamin C in the preparation is 1-14.3 g/L.

2. The method according to claim 1, wherein concentration of the purified melatonin is 2.32 g/L.

3. The method according to claim 1, wherein concentration of the vitamin C is 8.8 g/L.

4. The method according to claim 1, wherein the antioxidant preparation is produced by a method comprising dissolving vitamin C in 75% ethanol solution followed by addition of melatonin, the operation process being carried out in dark.

5. The method according to claim 1, wherein the concentration of the purified melatonin in the preparation is 2.32 g/L and the concentration of the vitamin C in the preparation is 8.8 g/L.

* * * * *